United States Patent [19]
McDonald

[11] Patent Number: 6,146,388
[45] Date of Patent: *Nov. 14, 2000

[54] ROCKING APPARATUS FOR MANIPULATING ELEMENT IN THE EYE

[75] Inventor: Henry H. McDonald, Rancho Mirage, Calif.

[73] Assignee: Surgical Concepts, Inc., Newport Beach, Calif.

[ * ] Notice: This patent is subject to a terminal disclaimer.

[21] Appl. No.: 09/337,441

[22] Filed: Jun. 21, 1999

[51] Int. Cl.⁷ .................................................... A61F 9/00
[52] U.S. Cl. ............................................................. 606/107
[58] Field of Search .................................. 606/107, 106, 606/157, 210, 211, 206, 207, 208, 133; 132/277, 280

[56] References Cited

U.S. PATENT DOCUMENTS

| | | | |
|---|---|---|---|
| 1,308,833 | 7/1919 | Armstrong | 132/277 |
| 1,823,685 | 9/1931 | Haims | 132/277 |
| 2,114,695 | 4/1938 | Anderson | 606/206 |
| 4,318,313 | 3/1982 | Tartaglia | 606/207 |
| 5,135,530 | 8/1992 | Lehmer | 606/107 |
| 5,254,131 | 10/1993 | Razi | 606/208 |
| 5,292,324 | 3/1994 | McDonald | 606/107 |
| 5,499,997 | 3/1996 | Sharpe et al. | 606/206 |
| 5,766,189 | 6/1998 | Matsuno | 606/157 |
| 5,776,139 | 7/1998 | McDonald . | |
| 5,843,121 | 12/1998 | Yoon | 606/206 |
| 5,893,853 | 4/1999 | Arnold | 606/133 |

*Primary Examiner*—Jeffrey A. Smith
*Assistant Examiner*—Eduardo C. Robert
*Attorney, Agent, or Firm*—William W. Haefliger

[57] ABSTRACT

Apparatus used for intraocular manipulation of an element in an internal eye zone, as via a surgical incision in the corneo-scleral limbus, which includes two elongated lever arms, each of which has a distal first zone, a second pivot zone or zones rearward of said distal first zone, and a third manual pressure receiving zone, at least one of the arms having gripping structure protruding toward the other arm to enable gripping of the element between the first distal zones, the arms operatively coupled together rearwardly of the second zone or zones so that the first distal zones are yieldably urged toward one another by the arms to hold the gripped element therebetween, the second pivot zone or zones configured to pivot in interengagement in response to controllable manual squeezing force exertion on the third zones, thereby to cause the first zones to relatively separate, enabling movement of the arm and structure relative to the element.

28 Claims, 9 Drawing Sheets

ROCKING APPARATUS FOR MANIPULATING ELEMENT IN THE EYE

BACKGROUND OF THE INVENTION

This invention relates generally to manipulation of elements within the eye, and more specifically, concerns improvements in instruments used for this purpose. This invention improves upon that of U.S. Pat. No. 5,776,139 incorporated herein by reference.

There is need for further improvements in instrumentation used for this purpose; and in particular for improvements as are described herein, to provide unusual advantages as will appear.

SUMMARY OF THE INVENTION

It is a major object of the invention to provide improved instrumentating meeting the above-described need.

Basically, the herein-described apparatus is used for manipulation, elements within an internal eye zone, as via a surgical incision in the corneo-scleral limbus. Such elements may include artificial lenses, and hardened material that may develop in the eye. The apparatus basically includes:

a) two elongated lever arms, each of which has a distal first zone, a second pivot zone rearward of the distal first zone, and a third manual pressure receiving zone, at least one of the arms having gripping structure protruding toward the other arm to enable gripping of said element between the arm first distal zones, b) the arms operatively coupled together rearwardly of the second zone so that the first distal zones are yieldably urged toward one another by the arms to hold the gripped element therebetween, and, c) the second pivot zones configured to pivot in interengagement in response to controllable manual squeezing force exertion on said third zones, thereby to cause the first zones to relatively separate, enabling adjustable movement of the arms and gripping structure relative to said element.

As will be seen, interengageable protrusions are typically provided for projecting between the arms at the second zones, to define mutual fulcrums for arm pivoting. Such protrusions may have interengageable surfaces which are convex toward one another; and the protrusions are typically spaced apart prior to manual squeezing force exertion at the third zones, for reasons as will appear. Multiple such protrusions may be provided, whereby they operate at different times during controlled squeezing, for purposes as will appear.

Another object is to provide lever arms that have substantially the same configurations and that are mirror imaged, for simplicity.

Yet another object is to provide holder surfaces on said arms, offset from the third zones, to allow a physician to hold and manipulate the apparatus without inadvertent release of the gripped element, and before applying squeezing force that releases the element.

A further object is to provide for gripping of a plastic lens between the arm distal first zones; and typically, the lens may be folded in gripped condition, although the apparatus is usable for inserting non-folded lenses.

An additional object is the provision of a bow spring segment coupling the arms together, rearwardly of the described third zones, and exerting predetermined lens grip force via the arms, so that lens squeezing is not made a variable by physician-controlled squeezing of the lens, whereby lens damage is substantially lessened.

A further object is the provision of gripping structure on the arms, and that includes one of the following:

i) tapered protrusions on said arms, ii) protrusions on the arms that taper generally endwise of the arms, iii) protrusions on the arms that taper toward one another, iv) claws on the arms, and v) grippers on the arms Yet another object is to provide pivot zones that include:

i) primary and secondary pivot zones spaced apart along said arms, ii) whereby the primary pivot zones are operable in response to primary squeezing force exertion on said third zones and effect primary diverging of said arm distal first zones, and secondary pivot zone being inoperable at that time, iii) and whereby the secondary pivot zones are operable in response to secondary and increased squeezing force exertion on said third zone and effect secondary diverging of the arm distal first zones, accompanied by relative separation of said primary pivot zones.

An additional object is to orient the first distal zones to define a first plane, and said third zone projecting at an angle or angles, relative to said plane.

A yet further object it so provide holder structure for allowing the arms to controllably separate at the second pivot zones during relative separation of said distal first zones.

Another object is to provide guide means including a base for engaging the arms to effect controlled endwise displacement of said distal first zones relative to said base in response to controlled squeezing force exertion on the third zones.

An additional object is to provide an elongated pivot zone or zones, which may be convex along elongated zone length.

A yet further object is to provide method for using the apparatus as referred to.

These and other objects and advantages of the invention, as well as the details of an illustrative embodiment, will be more fully understood from the following specification and drawings, in which:

DETAILED DESCRIPTION

Figure 1:
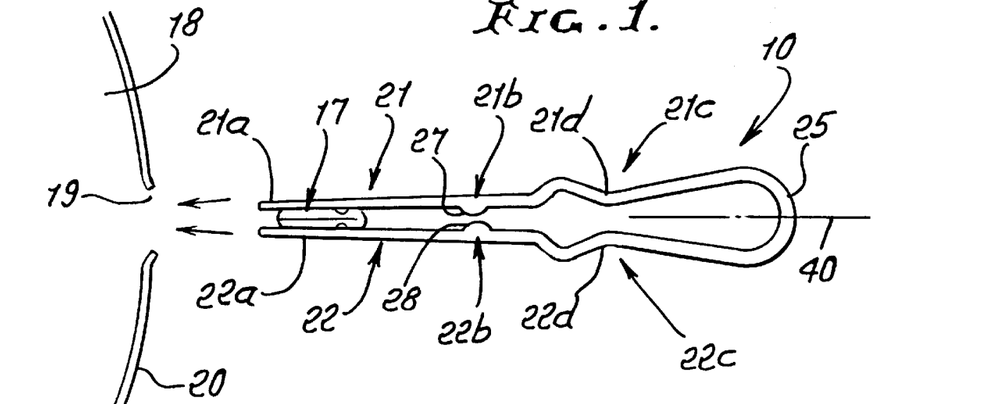
FIG. 1 is a side elevation showing a preferred embodiment, and an element gripped by the device.
Figures 1A, 2, 3:
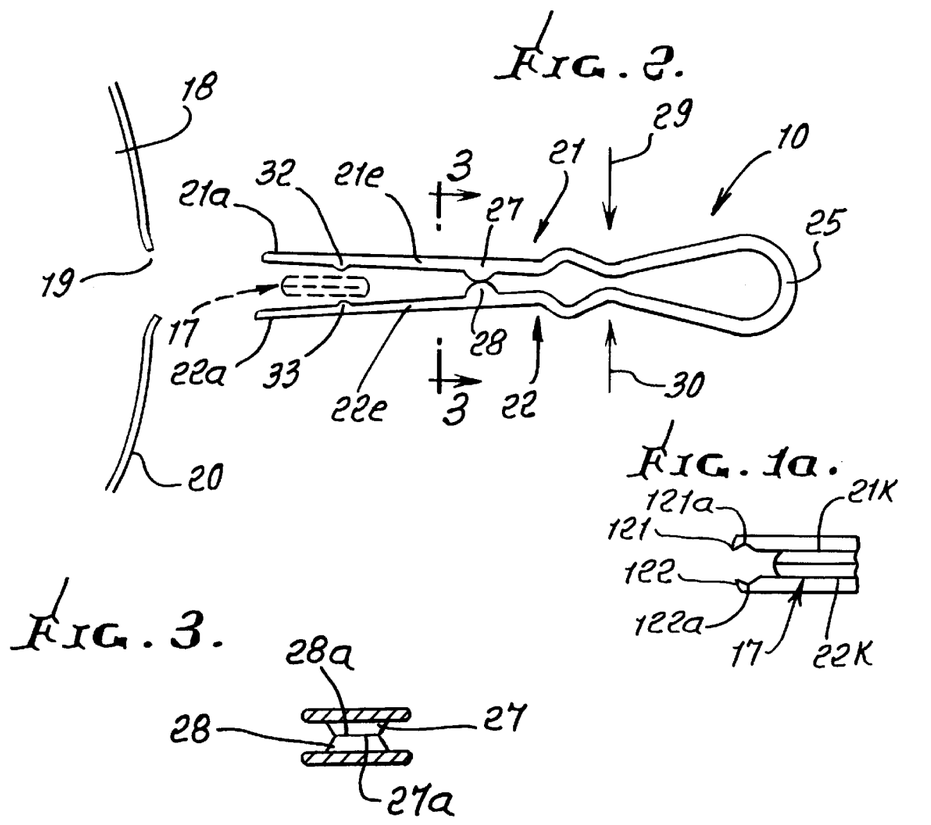
FIG. 1a is an enlarged view showing arms having angled grippers at their terminal ends.
FIG. 2 is a view like FIG. 1 but showing manual force application to cause element release.
FIG. 3 is a section taken on lines 3—3 of FIG. 2.
Figure 10:
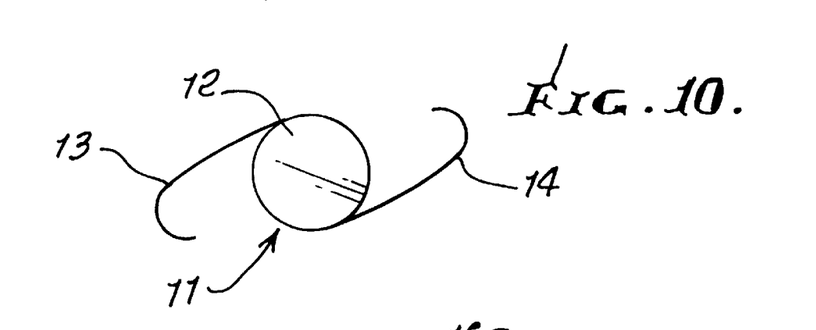
FIGS. 10 and 11 show foldable intraocular plastic lenses of types that can be implanted using the described apparatus.
Figure 11:
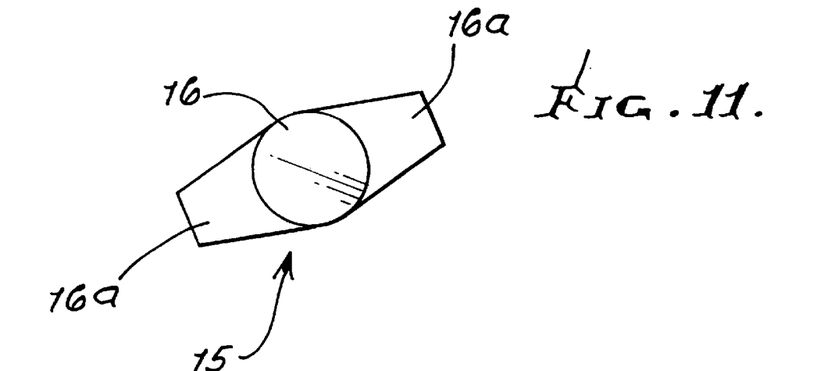

In FIGS. 1 and 2, the device or apparatus 10, i.e., instrument, is used for intraocular implantation of a plastic lens. Typical lens units are shown in FIGS. 10 and 11, others being usable. See for example my U.S. Pat. Nos. 5,203,789, 5,203,790 and 5,425,759, incorporated herein by reference.

In FIG. 10, a lens unit 11 has a lens zone 12, and two filamentary haptics 13 and 14.

In FIG. 11, the lens unit 15 has a lens zone 16, and two tabular or plate-like haptics 16a, for centering the unit in the eye.

A single folded lens unit is shown at 17 in FIG. 1, to be implanted in the eye interior 18 via a surgical incision 19 in the corneo-scleral limbus 20. The folded lens is gripped between and by two elongated lever arms 21 and 22. Arm 21 has a distal first zone 21a, and arms 22 also has a distal first zone 22a; and the lens is gripped between those arm zones. As also shown in FIG. 1a the arms also have irregular grips 121 and 122 angled and tapering inwardly toward one another at the arm ends for enhanced positive claw action gripping of elements such as a lens or pieces of eye structure to be inserted into the eye, or withdrawn from the eye. More precise positioning of the gripped element relative to eye structure is thereby achieved, as during rocking manipulation. Also note recesses 121a and 122a. See also FIGS. 15a and 15b described later. Arm surfaces 21k and 22k near the grips are smooth, as shown.

Arm 21 also has a pivot zone 21b rearward of and spaced from the distal zone 21a; and a third manual pressure-receiving zone 21c rearward of and spaced from the pivot zone 21b. Likewise, arm 22 has a pivot zone 22b rearward of and spaced from zone 22a, and a third manual pressure-receiving zone 22c rearward of and spaced from its pivot zone 22b. Such third zones 21c and 22c may be defined by arm segments that project toward one another, as shown, along the arm length, whereby a physician's fingers, or finger and thumb, may be easily received in and positioned by the dished or shallow pocket areas 21d and 22d, for precision control of the instrument 10 as it is used during lens implantation.

The arms are typically coupled together rearwardly of said third zones, so that the first distal zones 21a and 21b are yieldably urged toward one another by the arms to lightly but firmly grip the lens therebetween for implantation, as seen in FIG. 1. As shown, the arms are interconnected by bowed spring metal segment 25 at the rearward extents of the arms.

The said second pivot zones are configured to pivot in interengagement in response to controllable manual squeezing force exertion on the third zones 21c and 22c, thereby to cause said first zones 21a and 22a to relatively separate, freeing the lens for release in the internal eye zone. See this condition, as shown in FIG. 2.

In the example shown, there are interengageable protrusions 27 and 28 projecting between the arms at said second zones, to define mutual fulcrums for arm pivoting. The protrusions, which may be integral with the arms, have interengageable surfaces 27a and 28a which are convex toward one another, and are spaced apart, as seen in FIG. 1, prior to manual squeezing force application (see arrows 29 and 30) at the third zones. Such squeezing brings the surfaces 27a and 28a into interengagement, followed by rocking apart of the arm forward segments 21e and 22e, to allow lens release. Instead, separation of surfaces 27a and 28a allows undisturbed spring force application via the arms to the lens-gripping arm zones 21a and 22a, for precision gripping of the lens. The protrusions are close enough together that the lens is not damaged by slightly increased gripping force exertion thereon just prior to interengagement of the rocking protrusions, and subsequent lens release.

FIG. 9, steps a), b), c) and d), show progressive positions of a typical lens 17 as it releases from the instrument 10. Pivot point protrusions 32 and 33 from the arms engage the opposite sides of the gripped lens, and act as fulcrums, for lens pivoting, as it is released and without damage to the lens. The arms 21 and 22 are shown to have substantially the same configurations that are mirror imaged with respect to a central plane 40. Note that the arms remain at opposite sides of that plane, i.e., they do not cross over one another.

Figure 4:
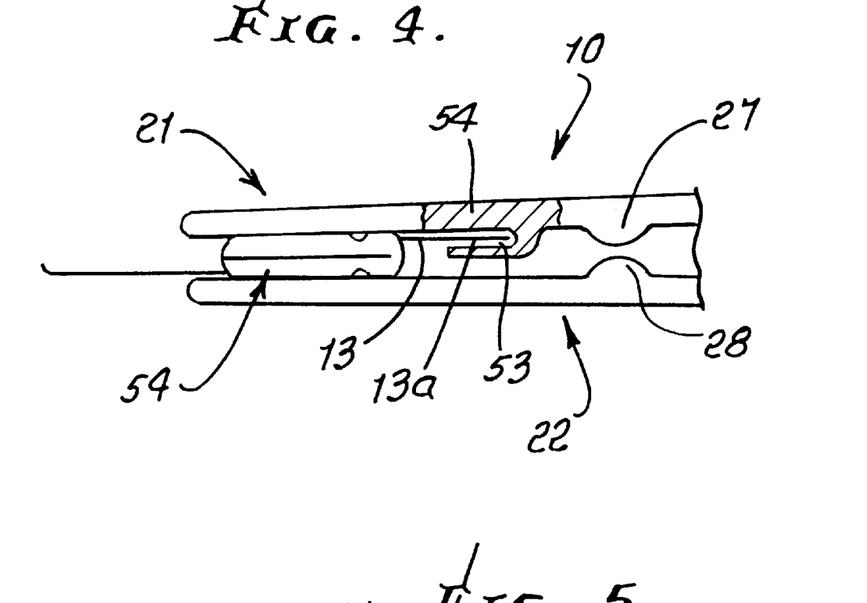
FIG. 4 is an enlarged fragmentary view of a modification showing retention of a haptic projecting from a lens gripped by the device.

FIG. 4 shows a modification wherein arm 21 has a small recess 53 formed in arm inner portion 54, for receiving the end portion 13a of a lens filamentary haptic 13, as referred to above. This controls the rear haptic position, as during lens implantation, and overcomes the problem of follow-up insertion of the rear haptic into the eye, after the lens itself has been positioned. As the released lens pivots away from the arms 21 and 22, the "trapped" rear haptic extent 13a moves out of the recess 53 and into desired position in the eye. If desired, recess 53 can be located in a protrusion 27 or 28. A single folded lens 54 is shown in FIG. 4.

Figure 5:
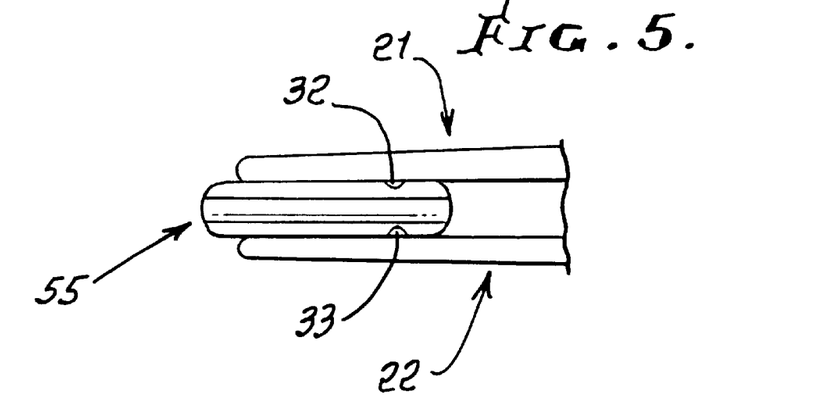
FIG. 5 is an enlarged fragmentary view showing gripping of a lens, which has multiple folds.
Figure 6:
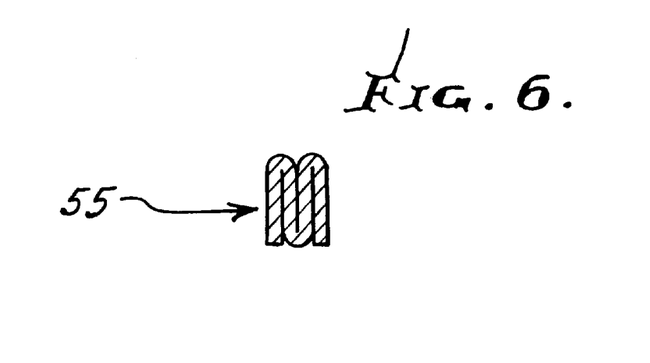
FIG. 6 is a section taken through the multiple folded lens of FIG. 5.

FIGS. 5 and 6 show a multiple folded lens 55 having M or W shape, as seen in FIG. 6. FIG. 5 shows that lens gripped by the instrument arms 21 and 22.

Figure 7:
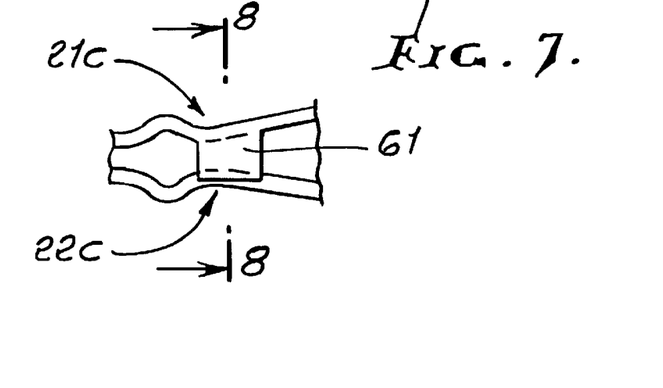
FIG. 7 is a fragmentary view of a modification in which alternate surfaces are provided on the device arms, to be gripped by a physician before the device is squeezed to release the lens.
Figure 8:
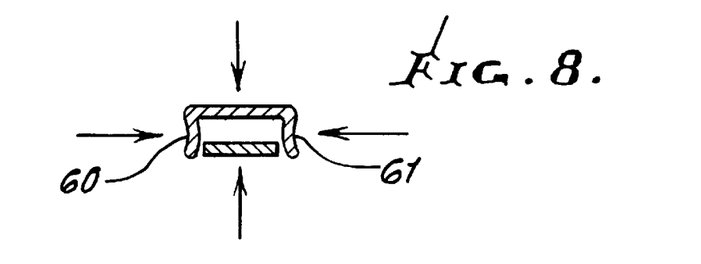
FIG. 8 is a section on lines 8—8 of FIG. 7.
Figure 9A:
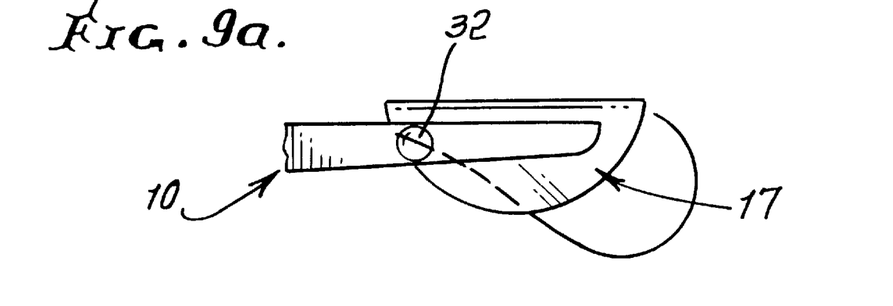
FIG. 9 views a) - - - d), show progressive stages of lens release, in side view.
Figure 9B:
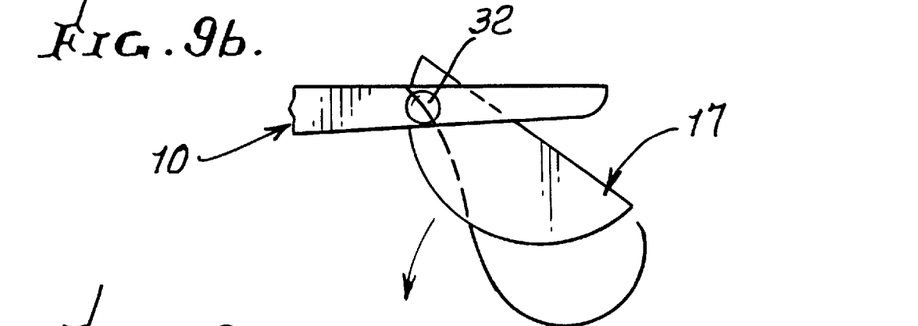
Figure 9C:
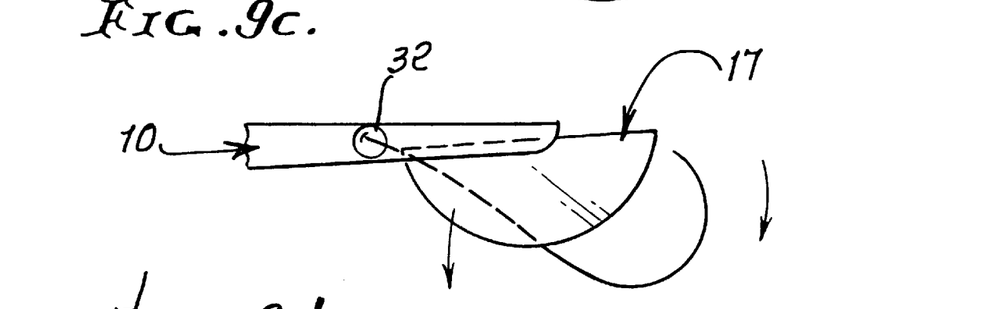
Figure 9D:
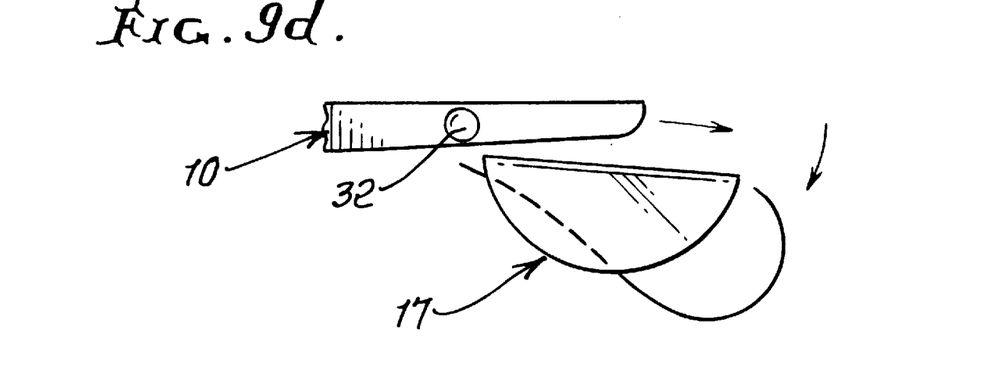

FIGS. 7 and 8 show laterally spaced flanges 60 and 61 on one or both arms at the third zone, to be gripped by the user physician, as during maneuvered insertion of the arm first zones into the eye, prior to lens release. Thus, the user does not inadvertently squeeze zones 21c and 22c during such insertion. Thereafter, the user can easily shift his finger positioning 90° to engage and squeeze zones 21c and 22d, to accomplish lens release at the appropriate moment.

In this regard, the amount of squeeze or pressure on flanges 60 and 61 is not determinative of lens release, allowing the physician use more latitude or flexibility in his use of the instrument, while enhancing or facilitating ultimate precision-timing of lens release.

The method of implanting the lens into an eye zone, using the apparatus described includes:

$x_1$) manipulating the arms to introduce the first arm zones and the lens gripped therebetween into the eye zone, and $x_2$) exerting manual pressure on such third zones, exteriorly of the eye, to effect arm pivoting and separation of said first zones, thereby to release the lens into the eye, x₃) the arms maintained at opposite sides of a plane extending through the lens and generally between the protrusions.

Figure 15A:
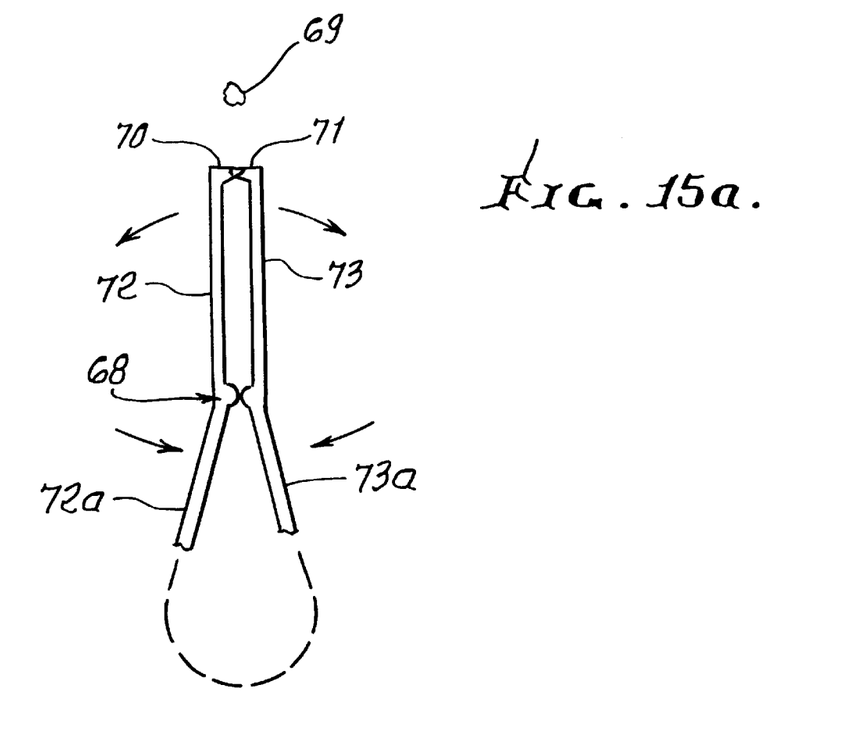
FIGS. 15a and 15b are views of different grippers at the arm distal first zones.

Referring now to FIG. 15a, it shows the provision of tapered protrusions or claws 70 and 71 on arms 72 and 73, for gripping an object or element, one example of which is a lens, as referred to above. Other examples are pieces 69 of eye structure such as phaco material, such as pieces, to be removed from the eye.

Figure 15B:
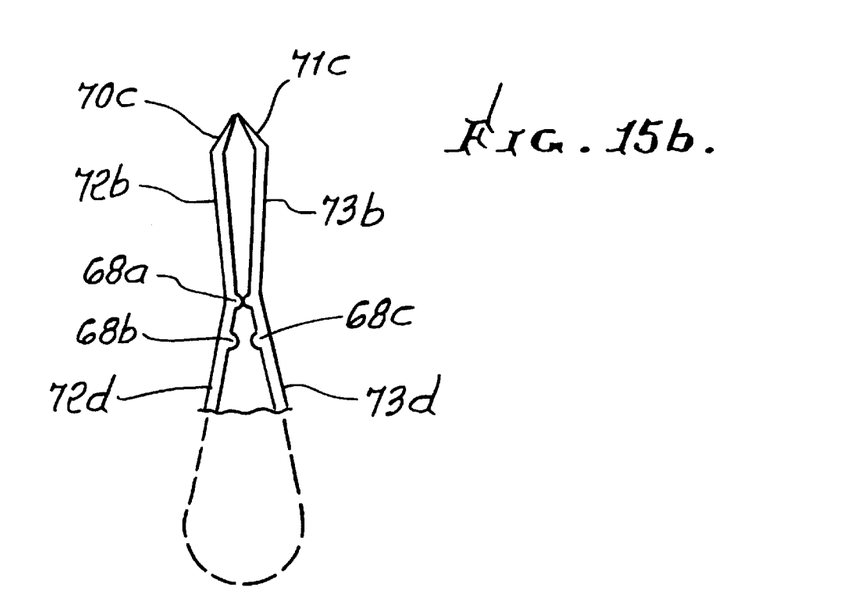

The protrusions are angled to project toward and taper toward one another, as in the form of gripper claws. The claws and arms 72 and 73 separate when arm extensions 72a and 73a are squeezed toward one another, to pivot at 68. FIG. 15b show modified tapered protrusions or claws 70c and 71c on the arms 72b and 73b which taper endwise of the arms, and also sidewardly toward one another. Distal claws 70c and 71c separate when arms 72b and 73b are squeezed, to rock or pivot at primary pivot location 68a, and separate further when secondary pivots 68b and 68c engage and rock, as arms 72d and 73d are further squeezed, causing arm separation at 68a. Other forms of irregular object or element grippers may be provided.

Figure 12:
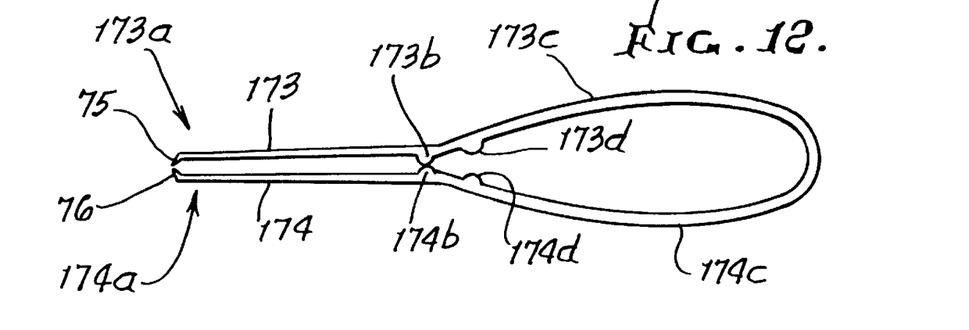
FIG. 12 is a side view of a modified embodiment, having both primary and secondary pivot locations.
Figure 13:
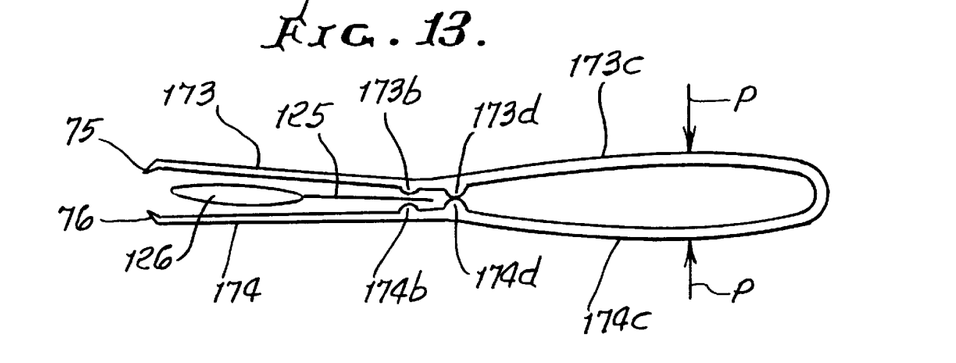
FIG. 13 is a view like FIG. 12 but showing pivoting about the second pivot location, to allow separation of pivot parts at the first location.

Referring now to FIGS. 12 and 13, a modified apparatus is shown, having arms 173 and 174, like arms 21 and 22, with distal first zones 173a and 174a that include tapered end grippers 75 and 76. Arm primary pivot zones are provided at protrusions 173b and 174b, like 21b and 22b; and bow spring shaped arm third (pressure P receiving) zones are provided at 173c and 174c. Also provided are arms secondary pivot zones at 173d and 174d, rearwardly spaced from 173b and 174b. As the arm zones 173c and 174c are squeezed toward one another, rocking or pivoting occurs first at protrusion zones 173b and 174b, as the arm distal zones 173a and 174a initially separate. Subsequently, as the arm zones 173c and 174c are further squeezed, the secondary pivot zone protrusions 173d and 174d come into rocking interengagement, and the first pivot zone protrusions 173b and 174b separate, as shown in FIG. 13. This effects release of any object or element portion or portions that may have become inadvertently caught (or intentionally returned or positioned) between 173b and 174b as upon initial grasping of the element by arm distal portions 173a and 174a. One example is a haptic attached to a lens to be gripped, and released in the eye. see haptic 125 and lens 126 in FIG. 13. In this way, the lens can be released first, and the haptic only released thereafter, so that if lens initial unfolding is incorrect, the lens can be retrieved since the haptic is still held, and complete release is only controllably achieved by pivoting at 173d and 174d.

Figure 14:
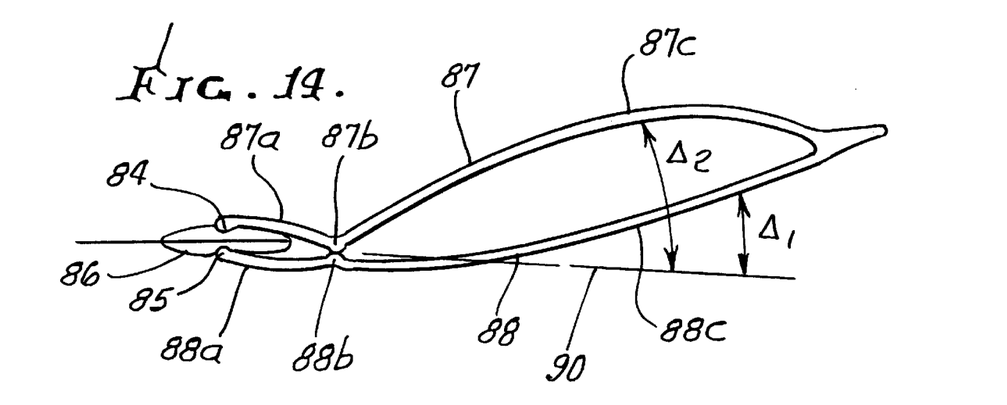
FIG. 14 is a side view of a modified embodiment showing angularity between the arm first zones, and the arm third zones.

FIG. 14 shows a modified apparatus the same as in FIG. 1 except for the provision of convex claw type grippers 84 and 85 protruding toward an object such as a folded lens 86, retained between arm 87 and 88 distal zones 87a and 88a. Arm rocking pivot zones appear at 87b and 88b, and interengage to allow separation of 87a and 88a in response to squeezing of pressure receiving zones 87c and 88c. The latter extend rearwardly and upwardly relative to a plane 90 generally defined by distal zones 87a and 88a. See arm angles $\Delta_1$ and $\Delta_2$.

Figure 16A:
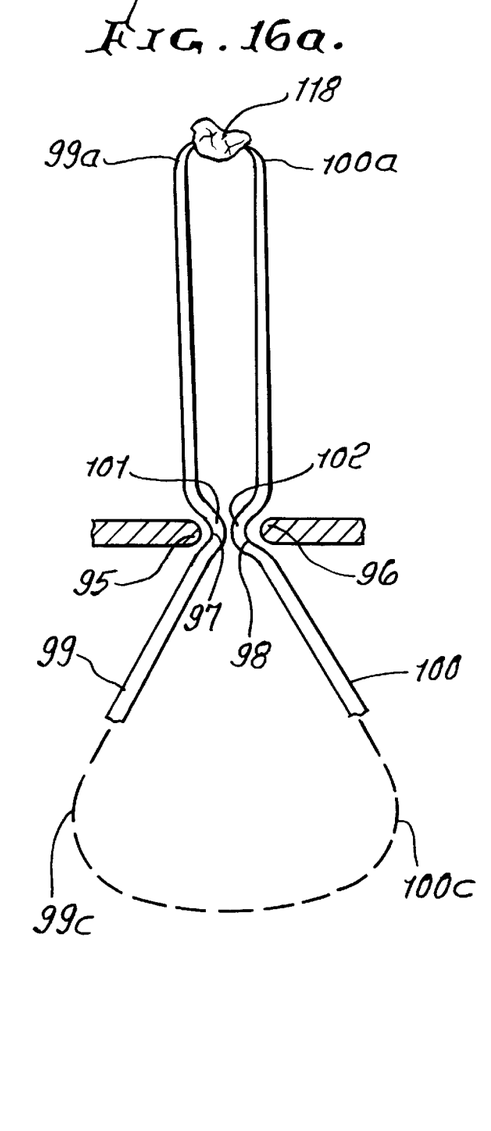
FIGS. 16a and 16b are views showing arm positioning proximate arm pivot zones.
Figure 16B:
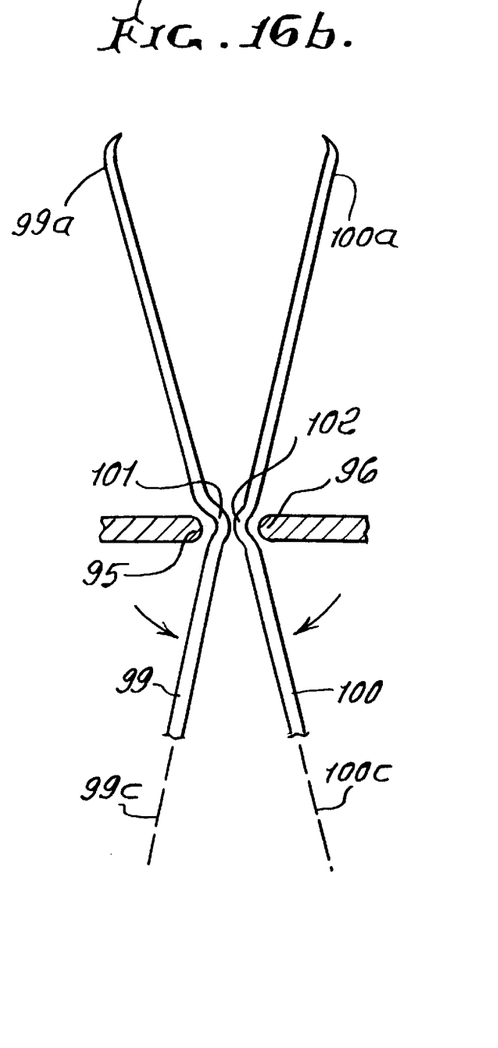

FIGS. 16a and 16b show the provision of holder protrusions 95 and 96 receivable in notches 97 and 98 formed in arm 99 and 100 pivot zone defining interengageable protrusions 101 and 102. Separation of the latter is thereby blocked, in response to squeezing of arm zones 99c and 100c, to effect separation of arm distal zones 99a and 100a as seen in FIG. 16b. Notches 97 and 98, form pivot bearings and acting to retain 101 and 102 in rocking engagement. A gripped element appears at 118, such as a piece of phaco material, and is released in FIG. 16b.

Figure 17A:
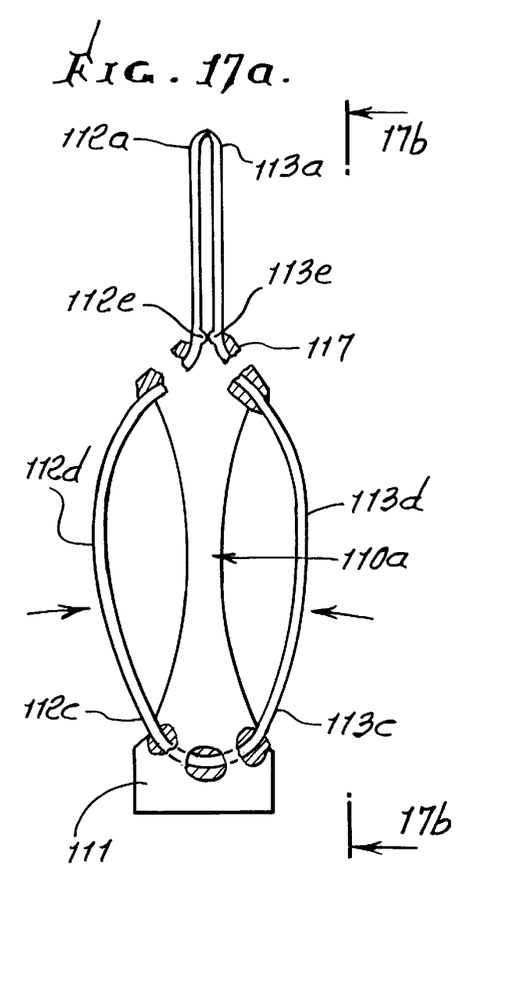
FIGS. 17a and 17b are front and side views of guide means to guide arm endwise displacement in response to squeezing force exertion.
Figure 17B:
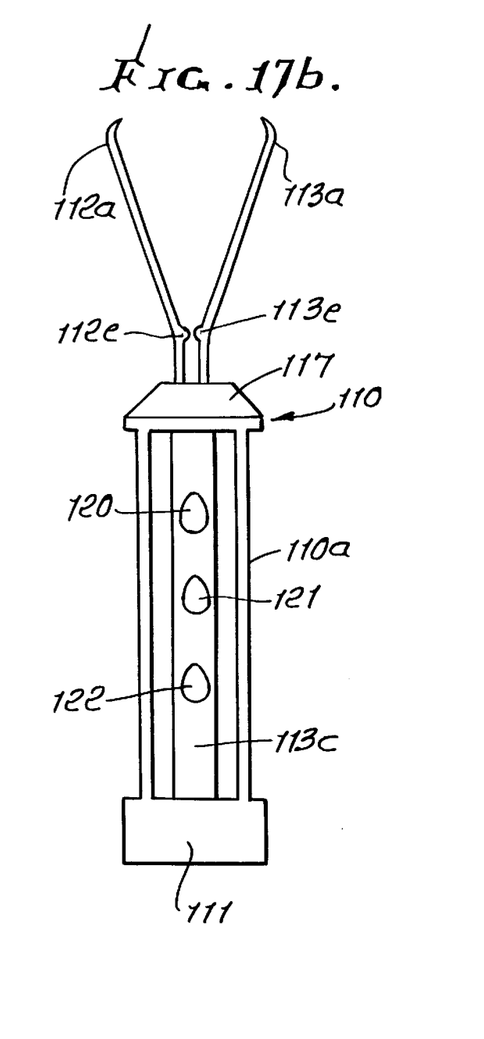

FIGS. 17a and 17b show a guide means 110 assembled to the dual arm apparatus, in any of its forms as described. It includes a base 111 to endwise position the end of the arm third zones, 112c and 113c. Upon squeezing of the exposed arm bow spring zones 112d and 113d, the first distal zones 112a and 113a are forwardly displaced relative to the base, as they rock and separate, and a forward guide portion 117 of the device 110 slidably engages the arms to guide them as they move forwardly. Device 110 incorporates struts 110a that provide a useful handle to be held by the user. Rocking pivots appear at 112e and 113e.

Multiple holder surfaces are formed on each arm, such as flats 120–122 seen in FIG. 17b.

Figure 18:
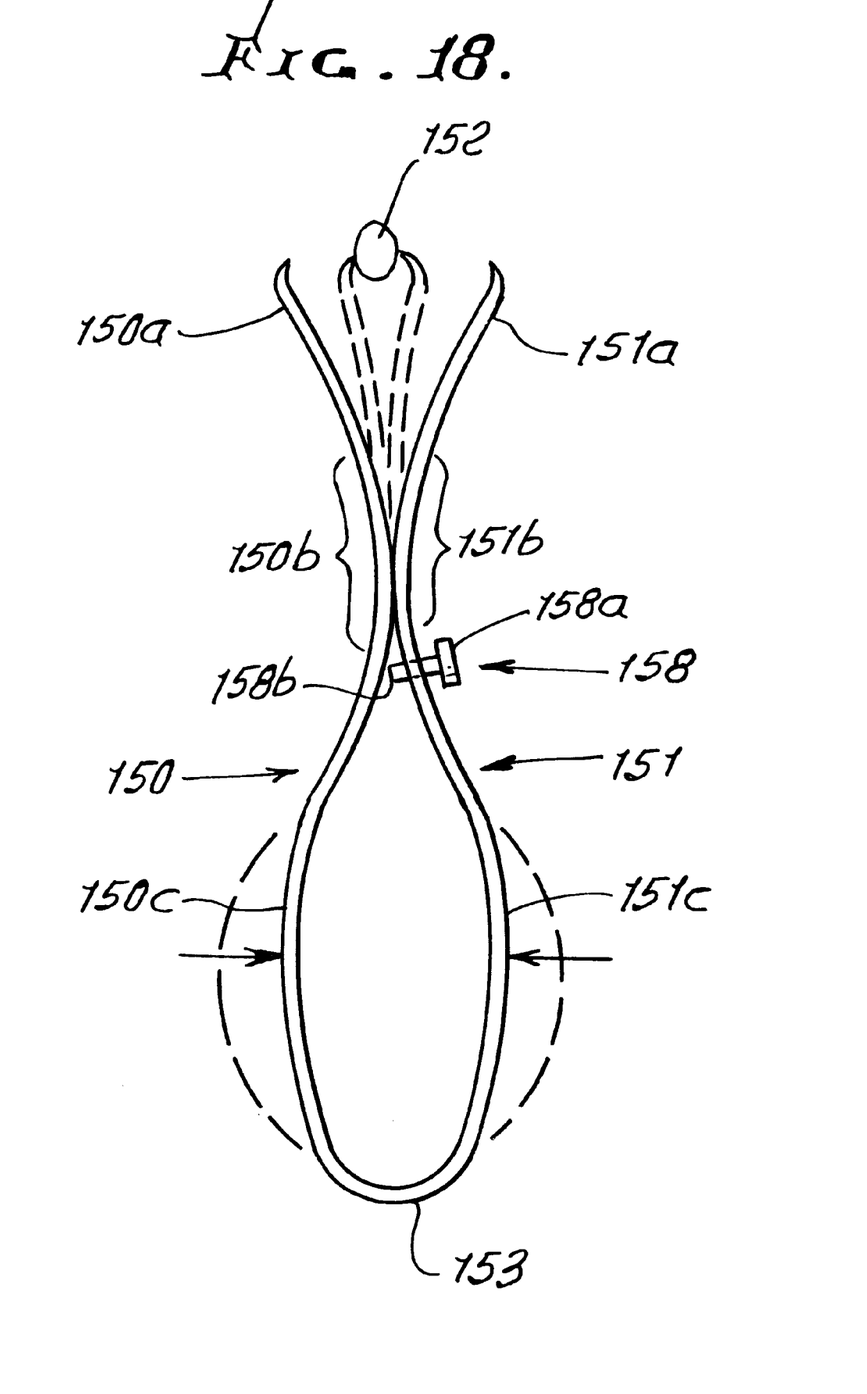
FIG. 18 shows a further modification.

FIG. 18 shows modified apparatus usable for intraocular manipulation of an element in an internal eye zone, as via a surgical incision in the corneo-scleral limbus, or usable for other purposes, and which includes:

a) two elongated lever arms 150 and 151 each of which has a distal first zone, an elongated and curved second pivot zone or zones rearward of said distal first zone, and a third manual pressure receiving zone. Such zones appear at 150a and 151a; 150b and 151b; and 150c and 151c. At least one of the arms has gripping structure protruding toward the other arm to enable gripping of an element 152 between the first distal zones, and which may for example incorporate terminal claws;

b) the arms are operatively coupled together, as at 153 rearwardly of said third zones so that the first distal zones are yieldably urged toward one another by the arms to hold the gripped element 152 therebetween. Coupling 153 may comprise a bow spring;

c) the elongated second pivot zone or zones 150b and 151b are configured to pivot in interengagement and at points progressively along their lengths in response to controllable manual squeezing force exertion on said third zones, thereby to cause the first zones 150a and 151a to accurately and progressively relatively separate, enabling accurate and controlled movement of said arm and gripped claw structure, relative to said element, for example to achieve controlled release of 152, or grasping of an element, such as an object in the eye, for removal. The elongated surfaces of 150b and 151b that face each other are lengthwise convex.

Accordingly, an accurately controlled progressive separation, or closure, of the arms is achieved, as for example by progressive pivoting between lengthwise pivot locations 150c and 151c, and 150d and 151d, otherwise representing the dual and spaced apart pivot locations as seen in FIGS. 12 and 13.

FIG. 18 also shows an adjustable stop 158 on one arm, that is engageable with the other arm to limit relative closure of the arms. The stop has a knob 158a that may be turned to adjust the screw threaded location of the stop shank 158b in or on the arm.

The broken lines indicate certain positions of the arms when reduced squeezing pressure is applied.

The accuracy of the FIG. 18 device enables its use in very small slits or wounds in the eye, during eye surgery, as for example about 2 mm slits or wounds.

I claim:

1. Apparatus used for intraocular manipulation of an element in an internal eye zone, as via a surgical incision in the corneo-scleral limbus, which includes:

a) two elongated lever arms, each of which has a distal first zone, a second pivot zone or zones rearward of said distal first zone, and a third manual pressure receiving zone, at least one of said arms having gripping structure protruding toward the other arm to enable gripping of an element between said first distal zones, b) said arms operatively coupled together rearwardly of said second zone so that said first distal zones are yieldably urged toward one another by said arms to hold the gripped element therebetween, c) said second pivot zone or zones configured to pivot in interengagement in response to controllable manual squeezing force exertion on said third zones, thereby to cause said first zones to relatively separate, enabling movement of said arm and structure relative to said element, d) said gripping structure comprising claw structure, e) said claw structure being at arm terminals, there also being smooth gripping protrusion surfaces on the arms, and spaced from said claws, whereby use of either said e) said claw structure being at arm terminals, there also being smooth gripping protrusion surfaces on the arms, and spaced from said claws, whereby use of either said smooth gripping protrusions surfaces, or said claw structure, is enabled, for gripping of different objects, f) said arms being entirely and everywhere at opposite sides of an elongated plane extending between the arms.

2. The apparatus of claim 1 wherein there are interengageable protrusions projecting between said arms at said second zones, to define mutual fulcrums for arm pivoting.

3. The apparatus of claim 2 wherein said protrusions have interengageable surfaces which are convex toward one another.

4. The apparatus of claim 2 wherein said protrusions are spaced apart prior to said manual squeezing force exertion at said third zones.

5. The apparatus of claim 1 wherein said lever
arms have configurations that are mirror imaged.

6. The apparatus of claim 1 including holder surfaces on said arms, offset from said third zones, to allow a physician to hold and manipulate the apparatus before applying said squeezing force.

7. The apparatus of claim 6 including multiple of such holder surfaces on each arm.

8. The apparatus of claim 1 including a bow spring coupling said arms together, rearwardly of said third zone.

9. The apparatus of claim 1 wherein said structure includes one of the following:
 i) tapered protrusions on said arms,
 ii) protrusions on the arms that taper generally endwise of said arms,
 iii) protrusions on the arms that taper toward one another
 iv) claws on said arms
 v) grippers on said arms.

10. The apparatus of claim 1 wherein said first distal zone defines a first plane, and said third zone projects at an angle or angles, relative to said plane.

11. The apparatus of claim 1 including holder structure for allowing the arms to controllably separate at said second pivot zones during relative separation of said distal first zones.

12. The apparatus of claim 11 wherein said holder structure engaging outer sides of the arms, proximate said second pivot zones.

13. The apparatus of claim 1 including guide means including a base for engaging said arms to effect controlled endwise displacement of said distal first zones relative to said base in response to controlled squeezing force exertion on said third zones.

14. The apparatus of claim 1 wherein at least one of said pivot zones on one arm is elongated generally lengthwise of the one arm on which it is located.

15. The apparatus of claim 14 wherein said elongated pivot zone is convex toward the other arm along the elongated length of the pivot tone or zones.

16. The apparatus of claim 15 including an adjustable stop carried by one of the arms to limit relative closure thereof.

17. The apparatus of claim 1 wherein said pivot zones on said arms are elongated generally lengthwise of said arms.

18. The apparatus of claim 17 wherein said elongated pivot zones are convex toward one another along their elongated lengths.

19. The apparatus of claim 1 including an adjustable stop carried by one of the arms to limit relative closure thereof.

20. In combination, a) two elongated lever arms, each of which has a distal first zone, a second pivot zone or zones rearward of said distal first zone, and a third manual pressure receiving zone, at least one of said arms having grippinq structure protruding toward the other arm to enable gripping of an element between said first distal zones, b) said arms operatively coupled together rearwardly of said second zone so that said first distal zones are yieldably urged toward one another by said arms to hold the gripped element therebetween, c) said second pivot zone or zones configured to pivot in interengagement in response to controllable manual squeezing force exertion on said third zones, thereby to cause said first zones to relatively separate, enabling movement of said arm and structure relative to said element, d) said gripping structure comprising claw structure, e) said claw structure being at arm terminals, there also being smooth gripping protrusion surfaces on the arms, and spaced from said claws, whereby use of either said smooth gripping protrusions surfaces, or said claw structure, is enabled, for gripping of different objects, f) said arms being entirely and everywhere at opposite sides of an elongated plane extending between the arms, g) and including said element gripped between said distal first zones, and by said structure, said element being manipulable in an internal eye zone, as via a surgical incision in the corneo-scleral limbus.

21. The combination of claim 20 wherein said element has one of the following configurations:
 i) U shaped lens
 ii) W shaped lens.

22. Apparatus used for intraocular manipulation of an element in an internal eye zone, as via a surgical incision in the corneo-scleral limbus, which includes:

a) two elongated lever arms, each of which has a distal first zone, a second pivot zone or zones rearward of said distal first zone, and a third manual pressure receiving zone, at least one of said arms having grippinq structure protruding toward the other arm to enable gripping of said element between said first distal zones, b) said arms operatively coupled together rearwardly of said second zone so that said first distal zones are yieldably urged toward one another by said arms to hold the gripped element therebetween, c) said second pivot zone or zones configured to pivot in interengagement in response to controllable manual squeezing force exertion on said third zones, thereby to cause said first zones to relatively separate, enabling movement of said arm and structure relative to said element, d) and wherein said pivot zones include
  i) primary and secondary pivot zones spaced apart along said arms,
  ii) whereby the primary pivot zone is operable in response to primary squeezing force exertion on said third zones to effect primary diverging of said arm distal first zone, and while the secondary pivot zone is inoperable,
  iii) and whereby the secondary pivot zone is operable in response to secondary and increased squeezing force exertion on said third zones to effect secondary diverging of said arm distal first zones, accompanied by relative separation of said primary pivot zone.

23. Apparatus used for intraocular manipulation of an element in an internal eye zone, as via a surgical incision in the corneo-scleral limbus, which includes:
  a) two elongated lever arms, each of which has a distal first zone, a second pivot zone or zones rearward of said distal first zone, and a third manual pressure receiving zone, at least one of said arms having gripping structure protruding toward the other arm to enable gripping of said element between said first distal zones,
  b) said arms operatively coupled together rearwardly of said second zone so that said first distal zones are yieldably urged toward one another by said arms to hold the gripped element therebetween,
  c) said second pivot zone or zones configured to pivot in interengagement in response to controllable manual squeezing force exertion on said third zones, thereby to cause said first zones to relatively separate, enabling movement of said arm and structure relative to said element,
  d) and including guide means including a base for engaging said arms to effect controlled endwise displacement of said distal first zones relative to said base in response to controlled squeezing force exertion on said third zones, said guide means including structure connected to said base and slidably engageable with bowed sections of said arms between said pivot zones and said base, in response to controlled squeezing force exertion on said bowed sections.

24. A method of manipulating an element in an intraocular zone, as via a surgical incision in the corneo-scleral limbus, which includes
  a) providing two elongated lever arms, each of which has a distal first zone, a second pivot zone or zones rearward of said distal first zone, and a third manual pressure receiving zone, at least one of said arms having gripping structure protruding toward the other arm to enable gripping of said element between said first distal zones,
  b) said arms operatively coupled together rearwardly of said second zone so that said first distal zones are yieldably urged toward one another by said arms for holding the gripped element therebetween,
  c) said second pivot zone or zones configured to pivot in interengagement in response to controllable manual squeezing force exertion on said third zones,
  d) and exerting controlled squeezing force on said third zones thereby to cause said first zones to relatively separate enabling movement of said arms and structure relative to said element, allowing release of said element,
  e) and wherein said second zones are provided to include
    i) primary and secondary pivot zones spaced apart along said arms
    ii) whereby the primary pivot zone is operable in response to primary squeezing force exertion on said third zones, to effect primary diverging of said arm distal first zones, and the secondary pivot zone is then inoperable.

25. The method of claim 24 including providing said structure to include one of the following:
  i) tapered protrusions on said arm
  ii) protrusion on the arms that taper generally endwise of said arms,
  iii) protrusions on the arms that taper toward one another,
  iv) claws on said arms
  v) grippers on said arms.

26. The method of claim 18 wherein said second zones are provided to include
  i) primary and secondary pivot zones spaced apart along said arms
  ii) whereby the primary pivot zone is operable in response to primary squeezing force exertion on said third zones, to effect primary diverging of said arm distal first zone, and the secondary pivot zone is then inoperable.

27. The method of claim 24 including providing holder structure allowing the arms to controllably separate at said second pivot zones during relative separation of said distal first zones.

28. The method of claim 27 wherein said holder structure is provided to engage outer sides of the arms, proximate said second pivot zones.

* * * * *